US010926449B2

(12) United States Patent
Ramani et al.

(10) Patent No.: US 10,926,449 B2
(45) Date of Patent: Feb. 23, 2021

(54) HEATER FOR FITTING ORTHOSES TO INDIVIDUAL BODY JOINT

(71) Applicant: Horsepower Technologies Inc., Lowell, MA (US)

(72) Inventors: Mouli Ramani, Andover, MA (US); Victoria Thompson, South Hamilton, MA (US); Kristin Jugenheimer Size, Waltham, MA (US); Richard L. Miller, Needham, MA (US); Evan Hunter Williams, Boston, MA (US); Andrew Jones, Roslindale, MA (US); Gregory Scott Torrisi, Midlothian, VA (US)

(73) Assignee: Horsepower Technologies Inc, Andover, MA (US)

( * ) Notice: Subject to any disclaimer, the term of this patent is extended or adjusted under 35 U.S.C. 154(b) by 528 days.

(21) Appl. No.: 15/932,109

(22) Filed: Feb. 5, 2018

(65) Prior Publication Data
US 2019/0240894 A1 Aug. 8, 2019

(51) Int. Cl.
*B29C 51/42* (2006.01)
*A01K 13/00* (2006.01)
(Continued)

(52) U.S. Cl.
CPC .......... *B29C 51/424* (2013.01); *A01K 13/007* (2013.01); *A61D 9/00* (2013.01);
(Continued)

(58) Field of Classification Search
CPC ......... A01K 13/007; A61D 9/00; A61F 13/00; A61F 13/046; A61F 13/066;
(Continued)

(56) References Cited

U.S. PATENT DOCUMENTS 3,848,286 A * 11/1974 Kahmann ................ A43B 1/10
    12/142 P
3,848,287 A * 11/1974 Simonsen ................ A43B 7/28
    12/142 P
(Continued)

FOREIGN PATENT DOCUMENTS

DE        10257144 A1 *  6/2004  ........... B29C 51/424
EP         1449497 A2 *  8/2004  ............... A61D 9/00
(Continued)

OTHER PUBLICATIONS

International Preliminary Report on Patentability on PCT PCT/US2019/016670 dated Aug. 20, 2020.
(Continued)

*Primary Examiner* — Grant Moubry
*Assistant Examiner* — Phillip Decker
(74) *Attorney, Agent, or Firm* — Foley & Lardner LLP

(57) ABSTRACT

An orthosis is fitted to a body joint, in a preferred embodiment the equine fetlock, by locating the center of rotation (COR) of the joint; measuring the bones comprising the joint at points located with respect to the COR; selecting the appropriate orthosis from a selection of models thereof; and custom-fitting the orthosis to the individual by heating it to soften a layer of thermoformable foam on the interior of the orthosis, and clamping the orthosis in place over the body joint. A kit of tools for performing the measurements is disclosed, as are a method for location of the COR of the body joint by palpation and a preferred heater.

4 Claims, 14 Drawing Sheets

(51) Int. Cl.
  *A61D 9/00* (2006.01)
  *A61F 5/01* (2006.01)
  *B29K 623/00* (2006.01)
  *B29K 675/00* (2006.01)
  *B29L 31/00* (2006.01)

(52) U.S. Cl.
  CPC .......... *A61F 5/0102* (2013.01); *A61F 5/0127* (2013.01); *A61F 2005/0165* (2013.01); *A61F 2005/0172* (2013.01); *B29K 2623/083* (2013.01); *B29K 2675/00* (2013.01); *B29L 2031/753* (2013.01)

(58) Field of Classification Search
  CPC .. A61F 2013/00187; A61F 2013/00634; A61F 5/00; A61F 5/01; A61F 5/0111; A61F 5/0102; A61F 7/02; B29C 51/242
  USPC .................................. 602/1, 2, 5, 46, 62, 65
  See application file for complete search history.

(56) References Cited

U.S. PATENT DOCUMENTS

| | | | | |
|---|---|---|---|---|
| 4,139,586 A * | 2/1979 | Gasson | ................ | B29C 33/046 264/2.7 |
| 4,964,229 A * | 10/1990 | Laberge | ................ | A43B 5/1666 36/93 |
| 5,042,464 A * | 8/1991 | Skwor | ................ | A43B 7/28 602/16 |
| 5,167,227 A * | 12/1992 | Meserlian | ................ | A61D 9/00 601/151 |
| 5,468,139 A * | 11/1995 | Stender | ................ | B29B 13/023 264/544 |
| 5,693,007 A * | 12/1997 | Townsend | ............. | A61F 5/0123 602/16 |
| 6,553,994 B2 * | 4/2003 | Bard | ........................ | A61F 5/01 128/845 |
| 7,559,910 B2 * | 7/2009 | Daly | .................... | A01K 13/007 119/817 |
| 8,075,506 B2 * | 12/2011 | Linares | ................ | A61F 13/046 602/14 |
| 8,303,527 B2 * | 11/2012 | Joseph | .................... | A61F 5/055 602/8 |
| 8,807,983 B2 * | 8/2014 | Petersson | ............... | B29C 51/28 425/389 |
| 9,427,347 B2 * | 8/2016 | Pflaster | ................ | A61B 5/1071 |
| 10,085,870 B2 * | 10/2018 | Pflaster | ................ | A61F 5/0127 |
| 2006/0231045 A1 * | 10/2006 | Lindley | ................ | A01K 13/007 119/856 |
| 2014/0039367 A1 * | 2/2014 | Boraas | .................. | A61F 5/0102 602/7 |
| 2015/0216703 A1 * | 8/2015 | Madden | ................ | A61F 5/0127 602/7 |
| 2016/0354223 A1 * | 12/2016 | Burns | .................... | A61F 5/0123 |
| 2017/0273397 A1 * | 9/2017 | Smith | .................... | A43B 7/141 |
| 2019/0239479 A1 * | 8/2019 | Ramani | ................ | A61F 5/0127 |

FOREIGN PATENT DOCUMENTS

| | | | | |
|---|---|---|---|---|
| WO | WO-2015/039191 A1 | 3/2015 | | |
| WO | WO-2019153001 A2 * | 8/2019 | .......... | A61B 5/1072 |
| WO | WO-2019153001 A3 * | 9/2019 | .......... | A01K 13/007 |

OTHER PUBLICATIONS

International Search Report and Written Opinion on PCT/US2019/016670 dated May 21, 2019.

* cited by examiner

HEATER FOR FITTING ORTHOSES TO INDIVIDUAL BODY JOINT

FIELD OF THE INVENTION

This invention relates to tools and methods for properly fitting orthoses to body joints. More specifically, this application relates to a heater for custom-fitting an orthosis to a body joint. A copending application relates to tools and methods for measurement of the body joint and selection of the correct orthosis from a selection thereof.

BACKGROUND OF THE INVENTION

It is well-known to employ orthoses fitting around body joints to assist in injury prevention, and for joint support for recovery after injury or surgery. The art shows many well-characterized classes of orthoses. It is self-evidently important that a given orthosis must properly fit the joint being treated so that the full therapeutic effect will be realized. Where the orthosis comprises, for example, cuffs secured to opposed members of a body joint meeting at a pivot point, and where the orthosis is designed to permit a degree of joint pivoting during rehabilitation or training, it is important both that the cuffs fit the opposed members, so that the orthosis does not slide out of position in use, and that the pivot point of the orthosis be aligned correctly with that of the joint, so that no improper forces are exerted on the body joint as it is extended and flexed.

One known class of orthosis is for limiting the range of motion of the equine fetlock joint. The fetlock joint connects the distal cannon bone (metacarpal bone III) to the proximal aspect of the long pastern bone (first phalanx) of the horse's leg (both fore and hind legs are considered to have fetlocks, although their detailed anatomy obviously varies somewhat). Both fore and hind fetlocks are subject to accident or injury, in particular due to hyperextension. An orthosis which limits the range of motion (ROM) of the fetlock can be very useful in preventing hyperextension and thus assisting in recovery from injury or surgery. An orthosis for this purpose for the fore equine fetlock is described in commonly-assigned application Ser. No. 14/545,799, filed Jun. 22, 2015. A comparable orthosis to aid in prevention of injury, e.g., during training could also be provided.

Object of the Invention

This application describes the invention in connection with fitting the orthosis of Ser. No. 14/545,799 to equine fetlocks, but is not limited thereto, nor to equine joints. In fact, the tools and methods of the invention may have applicability to the fitting of orthoses to a wide variety of body joints, including human. Furthermore, the invention is not limited to the fitting of orthoses for limiting the range of motion of the joint, but may be useful in fitting of orthoses for various clinical purposes. The invention may also find use in fitting of prostheses.

SUMMARY OF THE INVENTION

The present invention relates to fitting of an orthosis to a body joint involving a several-step procedure. First, the center of rotation of the joint is located, preferably using a palpation technique to identify various anatomical features of the joint. Specialized tools are used to measure the joint at key points. Next, these measurements are used to select the correctly-sized orthosis from a predetermined selection. Finally, the orthosis is custom-fit to the individual. The present application relates specifically to a heater that is used in a final custom-fitting step to heat and soften a thermoplastic inner layer of padding to allow it to be fitted to a specific animal.

BRIEF DESCRIPTION OF THE DRAWINGS

The invention will be better understood if reference is made to the accompanying drawings, in which.

DESCRIPTION OF THE PREFERRED EMBODIMENTS

The following describes the overall method of measuring key dimensions of a body joint and selecting the correct orthosis from a inventory thereof. The present application is directed to a heater that is used in a final custom-fitting stage.

As summarized above, the method of the invention involves four separate steps, performed in order: location of the center of rotation (COR) of the fetlock; measurement of key dimensions of the cannon, fetlock, and pastern, at points located with respect to the COR; selection of the appropriate orthosis from a selection of models thereof; and final fitting of the selected orthosis to the individual.

Figure 1:
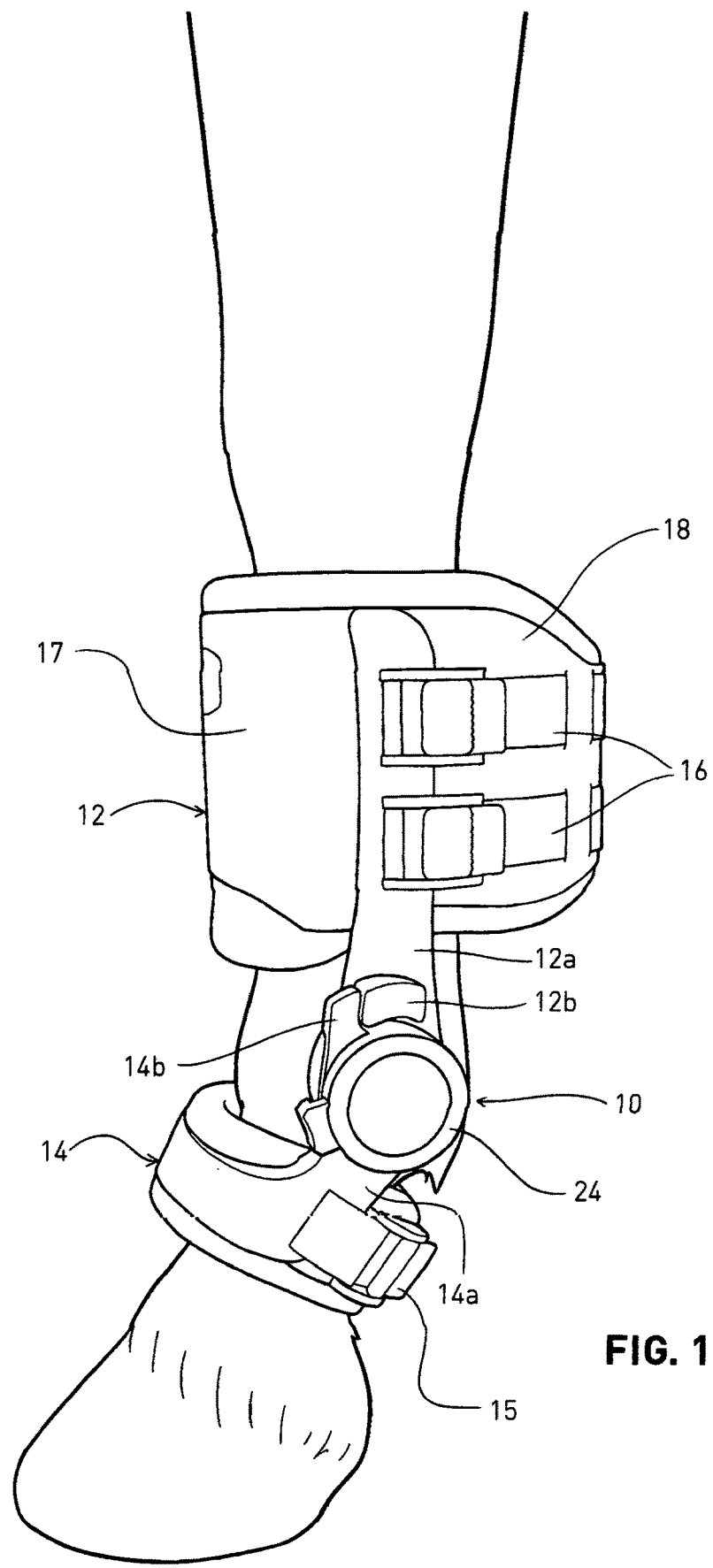
FIG. 1 shows a perspective view of the range of motion limiting orthosis disclosed in Ser. No. 14/545,799, as installed over a horse's left fore fetlock.
Figure 2:
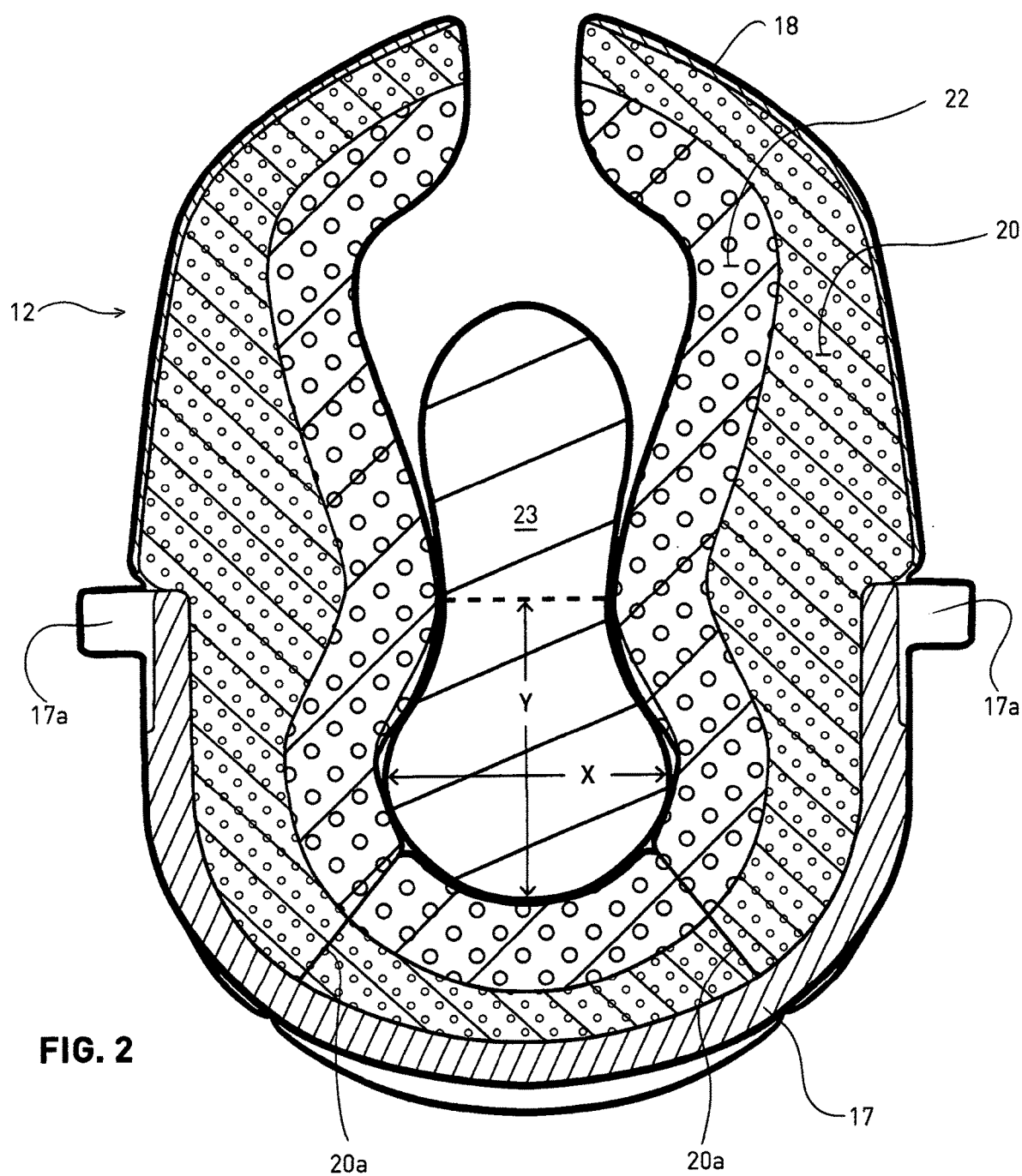
FIG. 2 is a cross-section through the orthosis at a point where it fits around the cannon bone, illustrating the different components thereof.

More particularly, the orthosis 10 used to limit the range of motion (ROM) of the fetlock disclosed in Ser. No. 14/545,799 is shown in FIG. 1 affixed to the left fore fetlock region (more specifically, to the cannon and pastern) of a horse. The orthosis 10 comprises an upper or proximal cuff 12 and a lower or distal cuff 14. As currently implemented, the proximal cuff 12 comprises a hard forward shell 17 and a rear outer sheath 18 of fabric or leather. The inner padding structure comprises an outer layer 20 (see FIG. 2) of molded polyurethane (PU) foam, and an inner layer 22 of thermoformable sheet foam, such as ethylene vinyl acetate (EVA). The proximal cuff 12 is secured to the cannon bone (including in "bone" the overlying fleshy structures, skin, and coat) by straps 16. The structure of the distal cuff 14 and its affixation to the pastern bone by strap 15 are similar.

The proximal cuff 12 is pivotally secured to the distal cuff 14 by lateral members 12a and 14a fixed to the respective cuffs. The lateral members 12a and 14a meet at a pivot structure 24, which may be as fully described in Ser. No. 14/545,799. Briefly, as the pastern rotates clockwise in FIG. 1, extending the fetlock joint, a stop 14b affixed to the distal cuff abuts a stop 12b affixed to the proximal cuff 12, limiting the ROM of the fetlock. The relative position of one or the other of the stops can be varied to limit the ROM to a desired degree. Again, see Ser. No. 14/545,799 for a preferred structure permitting this adjustment to be readily accomplished. Not seen in FIG. 1 are medial members corresponding to lateral members 12a and 14a which meet at a similar pivot structure, but lack the ROM stop mechanism, which is provided only on the lateral side of the orthosis 10.

The right-side orthosis is a mirror-image of that shown in FIG. 1. As noted, the pivot structures 24 allowing adjustment of the ROM of the fetlock are placed on the laterally-outer sides of the fetlocks, to avoid interference that would likely occur if this protruding structure were disposed on the medial inner side of the fetlock, especially noting that the orthoses are typically employed in pairs.

It will be apparent that in order to provide the maximal therapeutic function the cuffs must fit their respective bones closely and securely, so as to avoid slippage, and that the COR of the pivot structure of the orthosis must be substantially aligned with the COR of the fetlock, so as to achieve friction-free rotation and avoidance of unnatural pivoting of the fetlock.

The present invention is directed to achieving the good fit and accurate alignment mentioned above while providing the orthosis in a readily manufacturable form at reasonable cost. That is, although it would theoretically be possible to custom-fit a unique orthosis to each horse to be treated, this would be very time-consuming and inefficient. Moreover, the time taken to manufacture such a custom orthosis for a given horse might interfere with healing; that is, it would be preferred to have a number of premanufactured orthoses on hand for custom-fitting in a rapid fashion, so as to obtain the therapeutic effects thereof as rapidly as possible. An important aspect of the invention is therefore to provide a method for expeditiously determining which of a plurality of premanufactured orthoses is the best fit for a particular horse, and then to provide a method for rapidly custom-fitting the orthosis to the horse. However, as indicated above, the tools disclosed herein and employed for selecting the correct orthosis from a selection thereof could also be employed for making measurements useful in making custom-made orthoses.

As noted above, referring to FIG. 2, the proximal cuff 12 fitting over the cannon bone, shown approximately as a hatched section 23, comprises a forward shell 17 formed of plastic or metal, to which the straps 16 are attached, and to which the medial and lateral members 12a and 14a are riveted, and comprising bump-outs 17a on either side for alignment of the medial and lateral members, a thinner rear sheath 18 of fabric or leather, a first layer 20 of foam, e.g., polyurethane (PU) that is molded to define the basic inner contour of the cuff in contact with the cannon bone, and a second layer 22 of thermoformable sheet foam, of uniform thickness, and made of ethylene vinyl acetate (EVA) or the like. The foam layers may be made in several portions, as illustrated, and assembled with adhesive. The combination of the forward shell 17, rear sheath 18, and the molded PU layer 20 together define the "model" of the cuff, which is selected in response to the detailed measurement techniques described below. The cuff 12 is then custom fit to the horse by heating it, preferably in the specialized heater claimed in this application, until the EVA layer 22 is warmed sufficiently to be formable. The cannon cuff 12 is then placed quickly over the cannon bone and the straps 16 tightened. The pastern cuff 14 is fit similarly and simultaneously. As the EVA cools it hardens, so that its surface conforms to the outer surface of the respective bones. The heat content of the EVA is low, so that the horse is not burned painfully in the process. It should also be understood that a generally comparable technique employing a thermoformable foam is used for fitting ski boots to skiers' feet.

More specifically, the padding consists of two layers, an outer polyurethane (PU) foam layer 20 and an inner thermoformable foam layer 22. The PU foam layer 20 is injection-molded to define the shape of the inner contour of the cuff in a flat configuration with webs between the three sections in which it is molded, as indicated at 20a. The webs are either made sufficiently flexible that the PU layer 20 can be folded into its final shape, or the webs are removed and the parts are separated for later re-assembly. The thermoformable foam layer 22 is cut to shape and then heated and compression molded so as to follow the contours of the PU foam layer 20. The PU foam layer 20 and the thermoformable foam layer 22 are then laminated together using adhesive.

In order to prevent the top and bottom edges of the thermoformable foam layer 22 from flattening out during the heating and fitting process for the horse, its edges are stitched to small injection-molded pieces of elastomeric thermoplastic polyurethane (TPU) termed welts (not shown). Therefore, the complete process of assembling the thermoformable foam layer 22 is to (a) cut out the thermoformable parts, (b) stitch them to the welts and (c) laminate the welts and the thermoformable foam to the PU foam using adhesive. When the orthosis is fitted to the horse, the thermoformable foam maintains its outer contour due to the lamination but the inner contour changes to replicate the anatomy of the horse.

The provision of tooling to form the forward shell 17 is the most costly part of arranging for manufacture of the orthosis. Research has shown that the vast majority of horses can be accommodated with left and right shells 17 in a single size. The molded PU foam then defines the basic fit of the cuff over the cannon bone. Again, research has shown that the vast majority of horses can be accomodated if the molded PU is provided in four widths, dimension X in FIG. 2, where X is the maximum interior transverse dimension of an approximately oval forward section of the cuff, and two lengths, dimension Y in FIG. 2, the fore and aft dimension between the forwardmost surface of the oval forward section of the cuff and its narrowest point. Accordingly, 16 possible proximal cuffs are provided: 4 widths×2 lengths×2 (for left and right).

It has further been determined that there is some variation from horse to horse in the way in which the width of the cannon bone varies along its axial length. Therefore, as will be explained further below, its width is measured at three locations spaced from the COR, and the widest selected for the width X.

The distal pastern cuff 14 is structured and fit similarly, and is provided in 4 sizes, selected responsive to measurement of the circumference of the pastern at a given distance from the COR.

The medial and lateral members 12a and 14a are also provided in differing widths, corresponding to the width of the distal pastern cuff 14.

Thus a total of 128 models of the orthosis (16 proximal cuffs×4 distal cuffs×2 for left and right) is sufficient to fit the vast majority of horses.

Turning now to the method of fitting the orthosis to the horse, the first step is to locate the center of rotation (COR) of the fetlock, so as to ensure that the COR of the orthosis is correctly aligned with that of the fetlock. The COR is also used as the reference point from which the locations for most of the measurements needed are taken. The steps described in the following are but one way to locate the COR, and other methods of doing so are within the scope of the invention.

Figure 3:
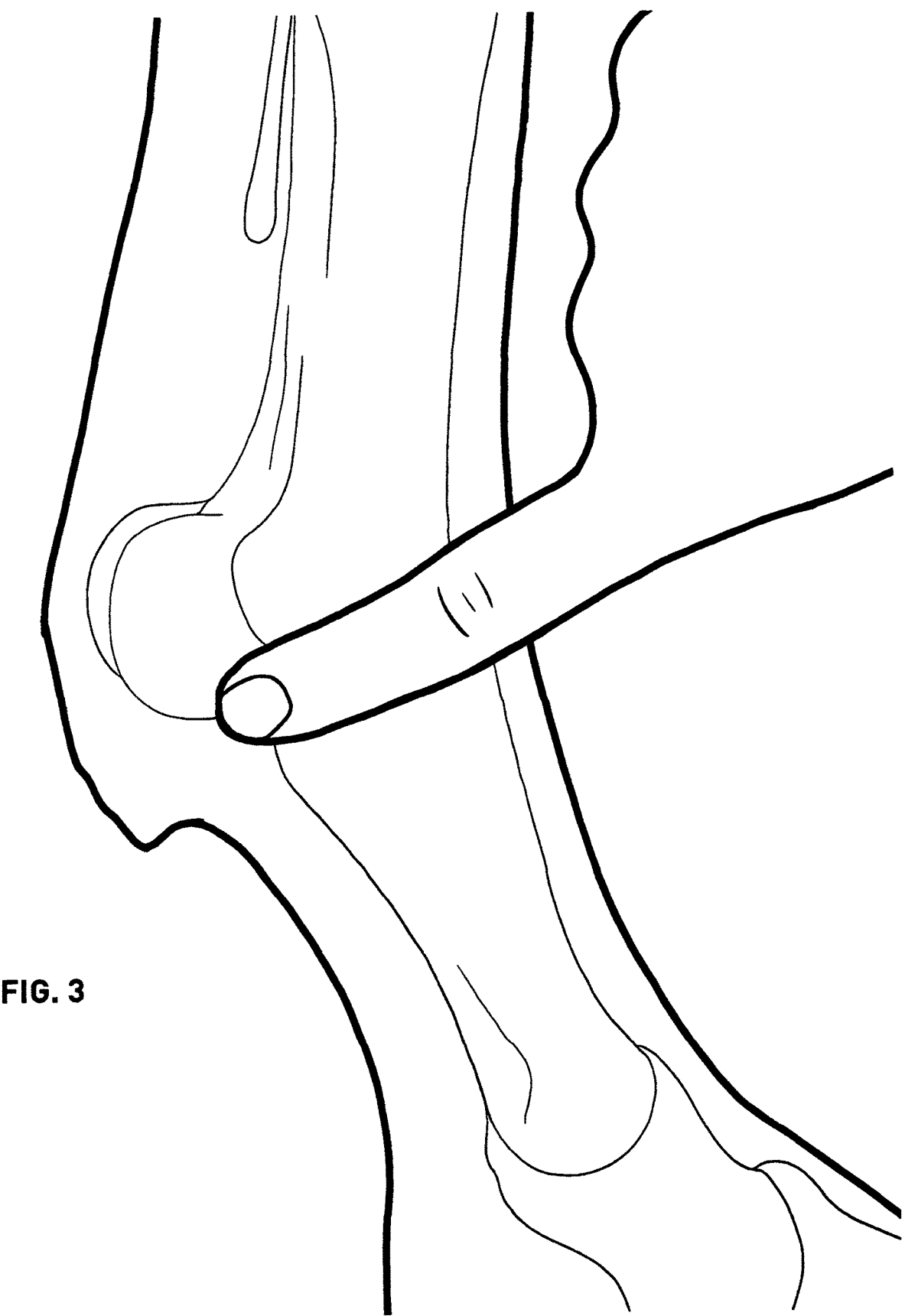
FIGS. 3-8 are perspective views of a horse's right fore fetlock, illustrating the steps performed in locating the center of rotation (COR) of the fetlock.

The first step is shown in FIG. 3, which illustrates the horse's right foreleg, with the bone contours shown by lighter weight lines. With the horse standing still on a flat firm surface, the user palpates the fetlock with the index finger and locates the depression between the palmar process of the first phalanx and the base of the ipsilateral (same side) proximal sesamoid bone. This can be identified as feeling like a "divot" on the surface of the fetlock.

Figure 4:
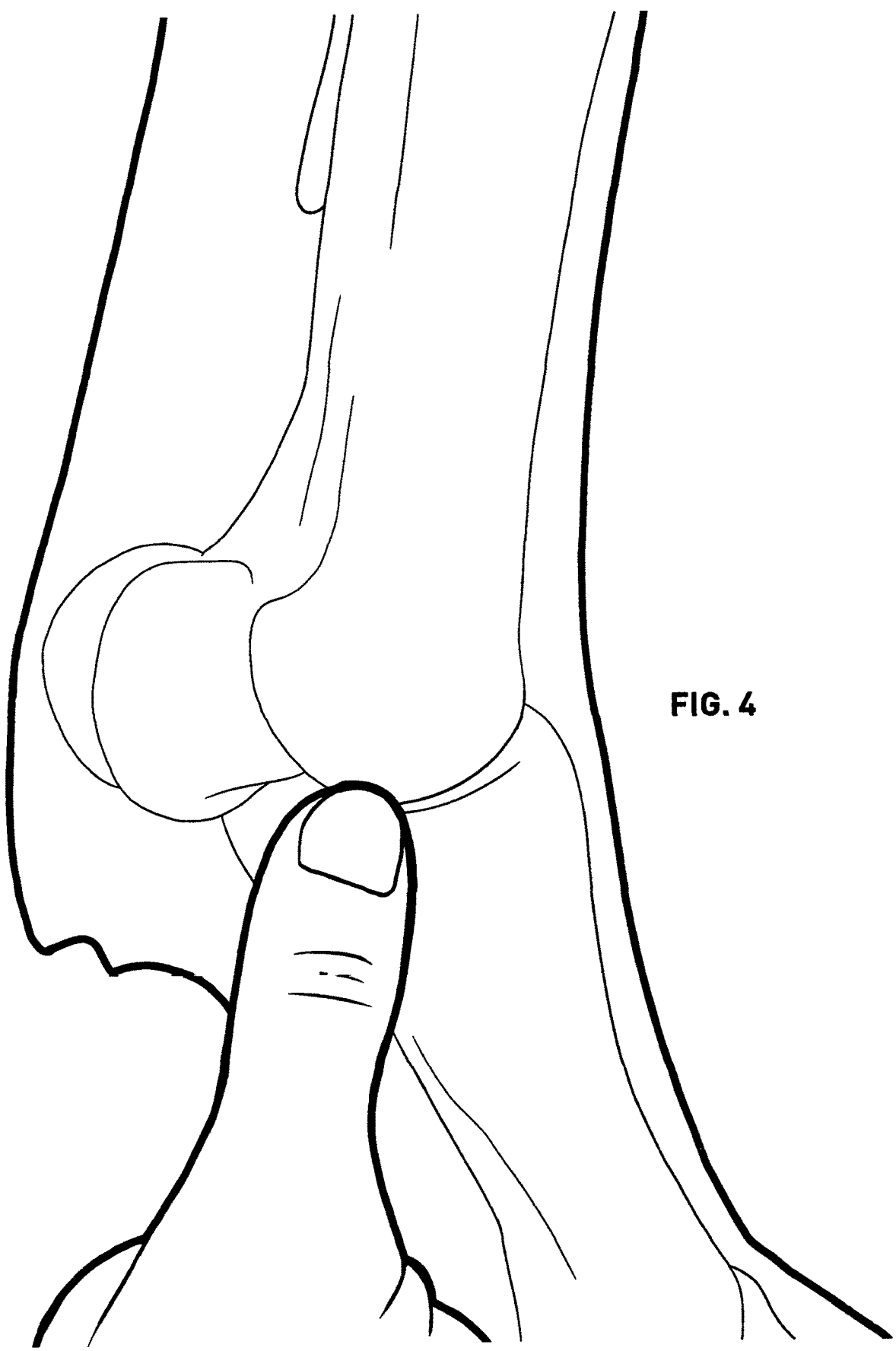
Figure 5:
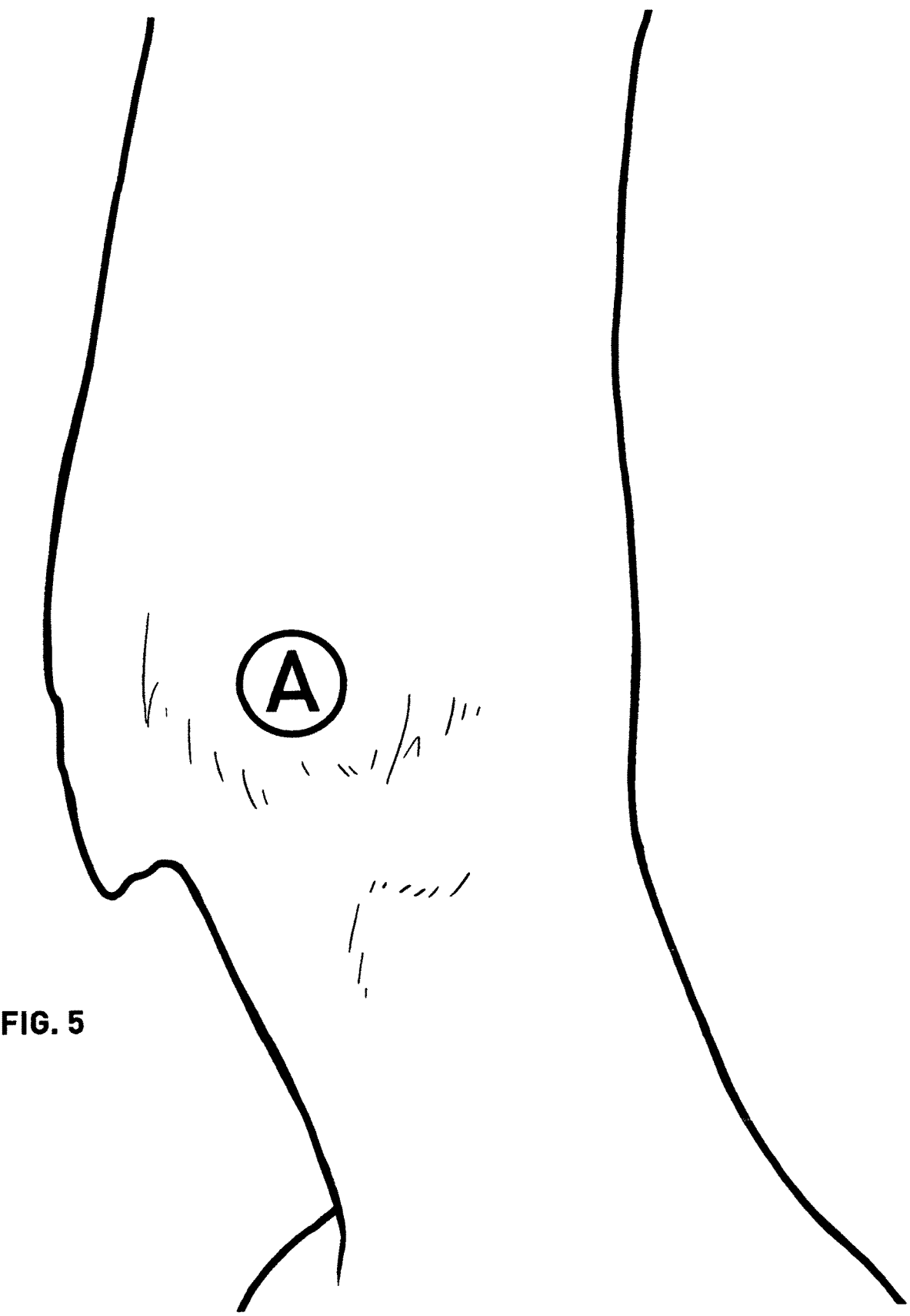

Next, as shown in FIG. 4, the user employs a thumbnail to identify the palmar-most (toward the rear of the horse) joint margin. As shown in FIG. 5, an adhesive marker, identified as marker A, is then applied to the joint at this point.

Figure 6:
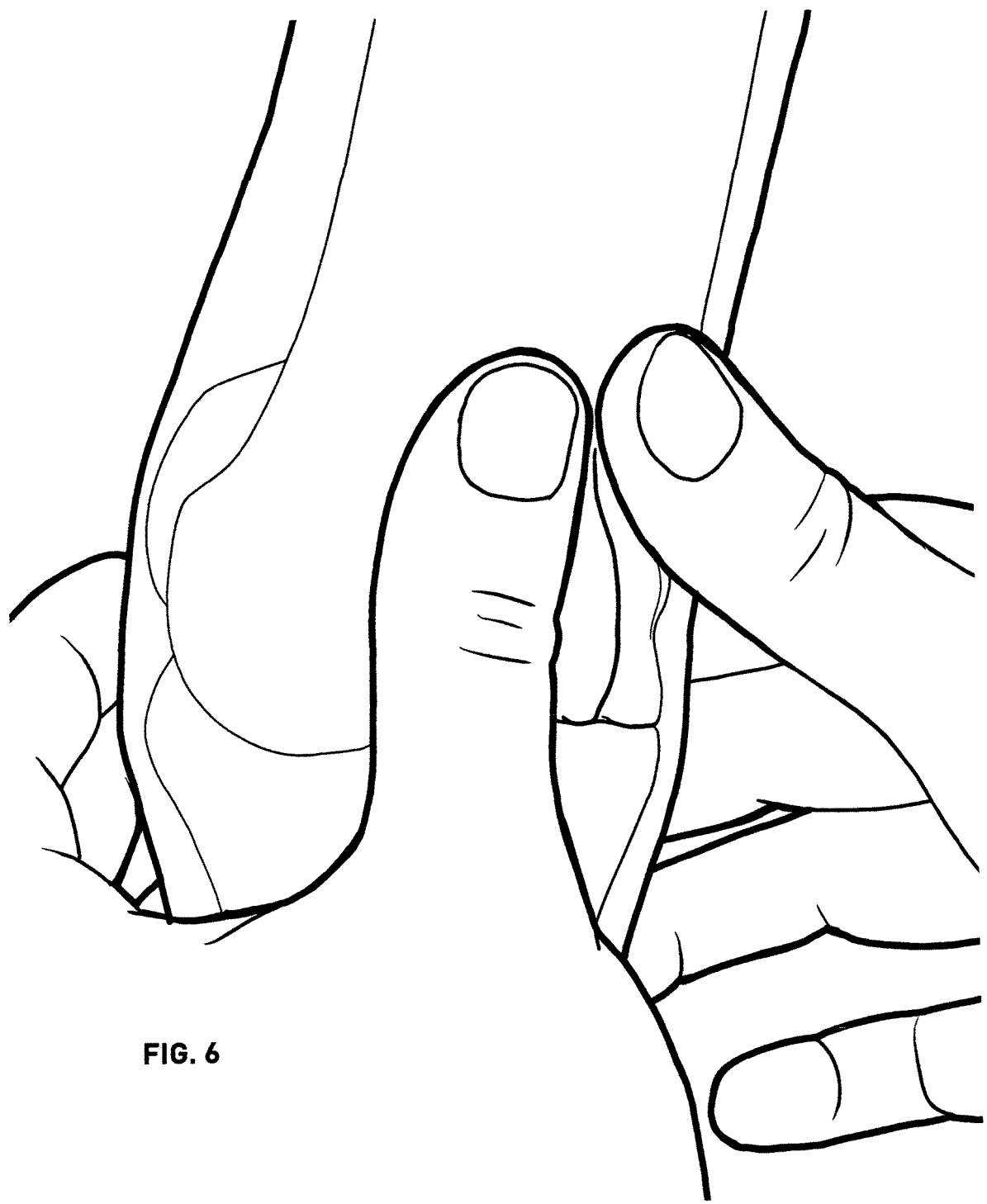
Figure 7:
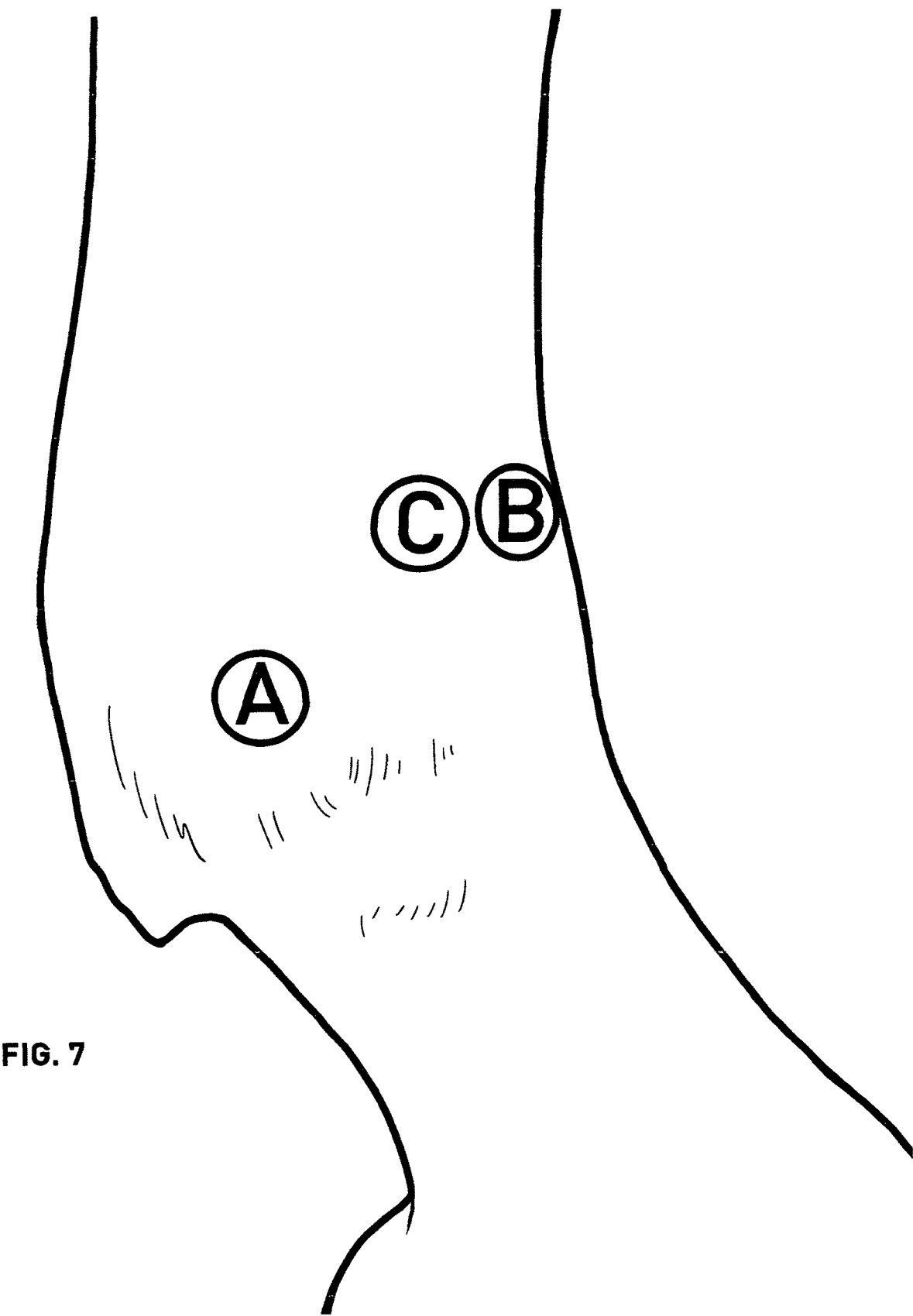

Next, as illustrated by FIG. 6, the user identifies the proximal-most prominence of the intercondylar ridge on the cranial aspect of the cannon near the fetlock. A marker B is placed where the intercondylar ridge merges with the flat cranial surface of the distal cannon bone. This point is identified by deeply palpating the front of the lower cannon bone with both thumbs, as illustrated. After marker B is placed at this point (see FIG. 7), a second marker C is placed at the same level with respect to the horizontal, but on the forward-most part of the lateral surface of the cannon bone. Again, see FIG. 7. Marker B can then be removed.

Figure 8:
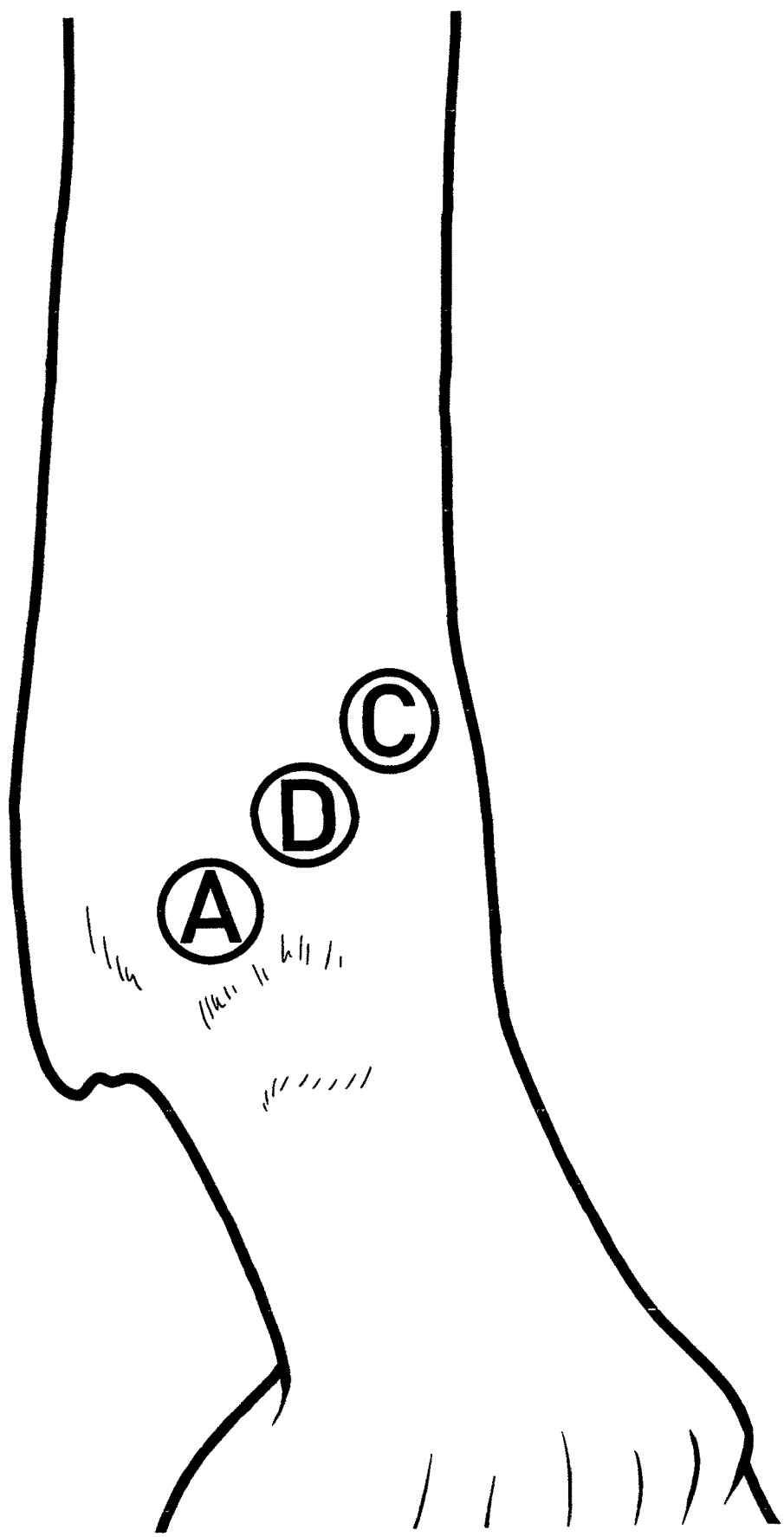

Finally, a fourth marker D is placed is placed midway between markers A and C, as illustrated by FIG. 8. This is the center of rotation (COR) of the fetlock. Markers A and C can then be removed.

The COR of the fetlock having thus been located, measurements can be taken using the COR as a "base point" from which the other measurement are located, ensuring that the orthosis thus fitted will have its COR substantially aligned with the COR of the fetlock.

Figure 9:
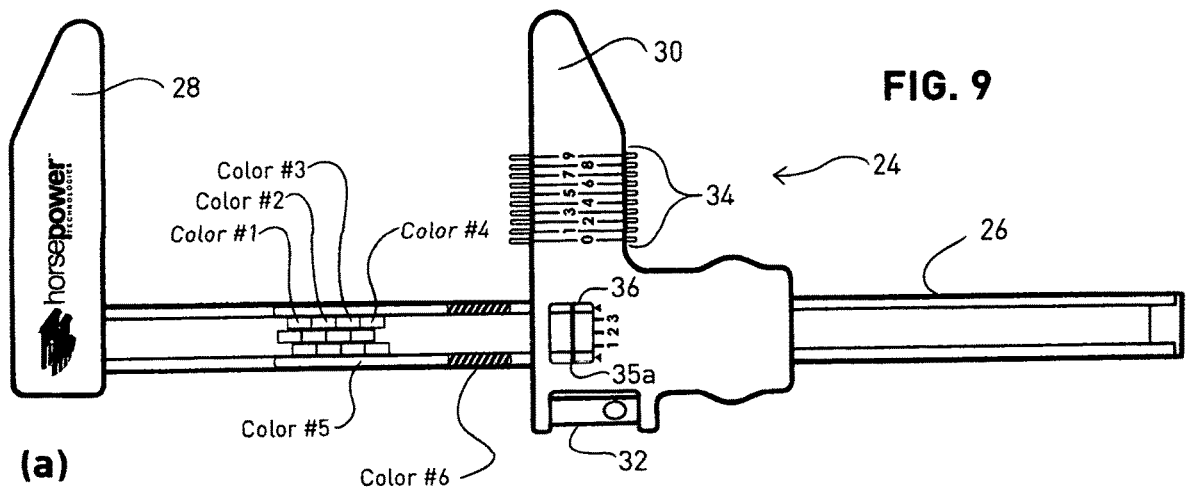
FIG. 9, comprising FIGS. 9 (a)-(e), shows views of the tools employed in the method of the invention, each being discussed separately below, these comprising a cannon tool, a pastern tool, an alignment tape, COR markers, and a measurement card, respectively.
Figure 9:
Figure 9:
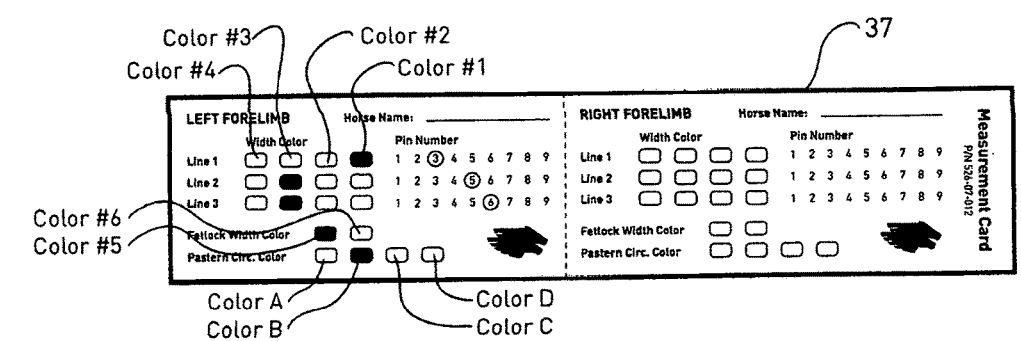

FIG. 9, including FIGS. 9 (a)-(e), shows a kit of tools provided by the proprietor of the orthosis to ensure proper fitting of the orthosis to the fetlock. It will be appreciated by those of skill in the art that comparable measurements could be made using different tools; those shown are but one convenient possibility. Further, several different embodiments of the tools shown could be employed; these will be discussed as appropriate.

Figures 11, 11A:
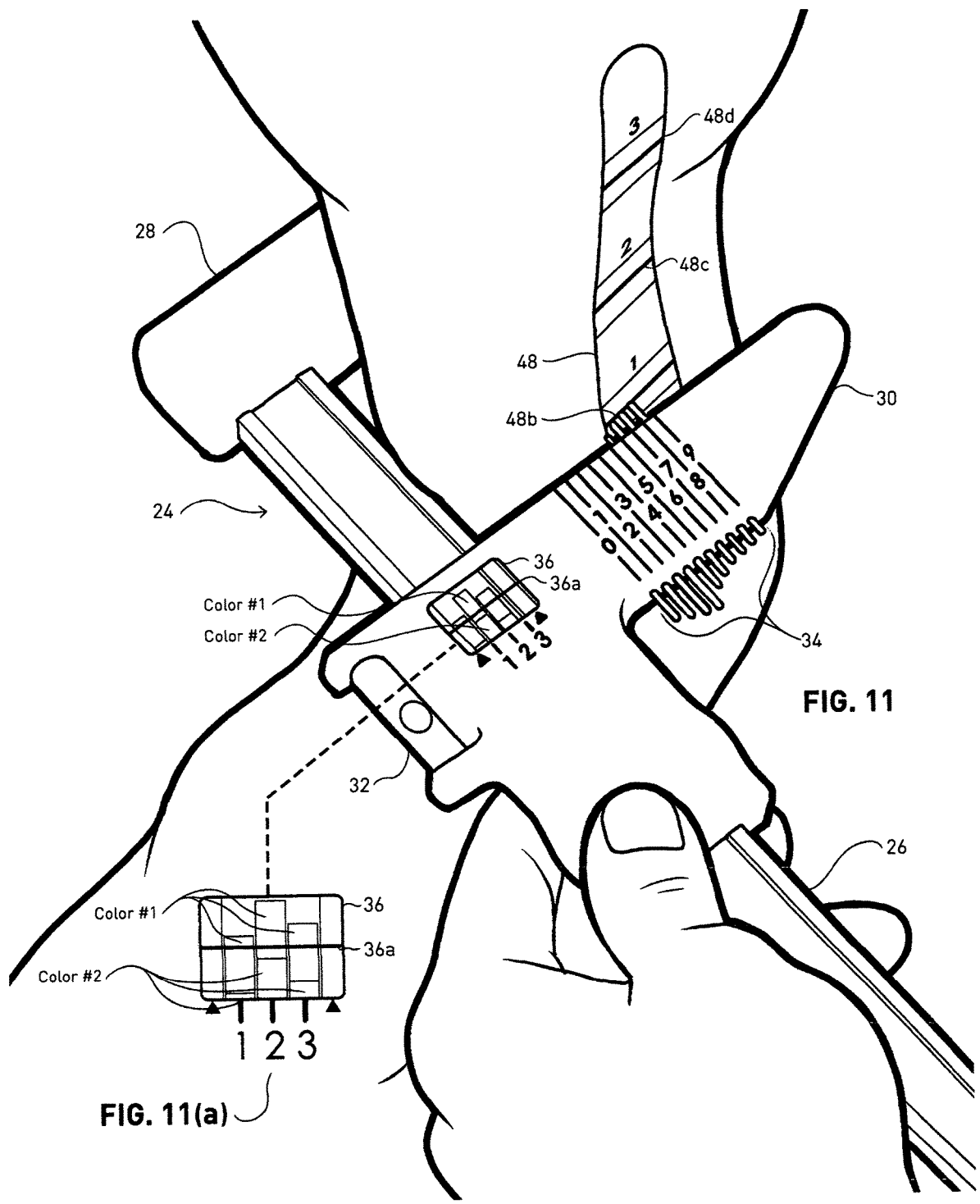
FIG. 11 shows a perspective view of the cannon tool in use to measure the width of the left cannon bone at one of three defined distances from the COR, and includes in FIG. 11 (a) an enlarged plan view of a measurement screen.

The cannon tool 24 shown in FIG. 9 (a) is used to measure the width X of the cannon bone and to locate the distance Y between the front of the cannon bone and its point of maximal width, which are important in selecting the proper model of the proximal cuff, as described above with reference to FIG. 2. The cannon tool 24 resembles a caliper, comprising a beam 26, a first anvil 28 fixed to one end of the beam 26, and a second anvil 30 sliding along beam 26. As illustrated by FIG. 11, and more fully discussed below, in order to measure the width of the cannon bone, the fixed anvil 28 is juxtaposed to one side of the cannon bone, with the beam held horizontal (as may be confirmed using a bubble level 32 mounted to the sliding anvil 30), in contact with the cannon bone, and square to the horse's centerline. The sliding anvil 30 is then brought into contact with the opposite side of the cannon bone. The distance between anvils 28 and 30 is then equal to the width X of the cannon bone. At the same time, a plurality of numbered pins 34 sliding in bores in sliding anvil 30, and spring-biased toward the inner surface of sliding anvil 30, that is, in the leftward direction in FIG. 9 (a), are brought into contact with the outer surface of the cannon bone. These pins are numbered, as indicated. One of the pins, located over the widest portion of the cannon bone, will protrude more than the others; its number is noted and used to specify the depth Y of the widest point of the cannon bone from its forward surface.

The distance X between the anvils during the measurement process may be determined in a variety of ways; for example, the beam 26 could be inscribed with inch or metric indicia, as in a conventional caliper. However, for reasons of convenience to the user, color-coded marks indicated by "colors 1-6" are printed on beam 26 of the cannon tool 24. A window 36 is formed in the sliding anvil 30, with a reference line 36a provided thereon. When a measurement is made, the color of the mark under the reference line 36a is noted, and a measurement card 37 shown in FIG. 9 (e) marked accordingly. The number of the pin that protrudes outwardly more than the others is also noted. The color-coding scheme employed in the preferred embodiment is described in connection with FIG. 11, below, as are details of the measurement process.

The cannon tool 24 is also used to measure the overall width of the fetlock, as described in connection with FIG. 12 below; this measurement is used to determine whether the orthosis is wide or narrow, that is, whether wide or narrow medial and lateral members 12a and 14a are needed.

The cannon tool 24 is provided with a second window on its opposite side, and the beam provided with a second set of colored marks, so that the tool 24 can be flipped over and used to make similar measurements of the opposite leg.

As discussed briefly above, the circumference of the pastern is measured in order to determine the proper combination of molded PU and thermoformable sheet foam to be provided in the distal cuff. A pastern tool 38, shown in FIG. 9(b), is provided for the purpose. This comprises a circular head portion 40 having an aperture 42 at its center. The pastern tool 38 is disposed on the pastern so that aperture 42 is located directly over the COR of the fetlock, that is, tool 38 is located so that marker D (FIG. 8) is disposed within aperture 42. A tongue 44 depends from head member 40, and a measuring ribbon 46 is secured thereto at a distance Z from the center of aperture 42. In use the ribbon 46 is passed around the pastern and the length of the ribbon 46 needed to circumscribe the pastern is noted. Again, this measurement could be made using conventional inch or metric indicia, but is preferably implemented using a color-coded system, as further detailed in FIG. 13 below.

FIG. 9 (c) shows an alignment tape 48 that is employed to locate three distances from the COR along the axial extent of the cannon bone at which measurements of the width and length of the cannon bone are made, as detailed below in connection with FIGS. 10 and 11. Tape 48 has an aperture 48a that in use is located over the COR of the fetlock. Tape 48 has an adhesive backing for allowing it to be conveniently secured to the cannon bone. A ring of hook and loop fastening material, nonwoven fabric or the like is preferably provided around the aperture 48a for attachment of the pastern tool 38, which is provided with a mating ring of mating material.

FIG. 9 (d) shows one of the adhesive markers 50 that are used in determination of the COR, as described above.

Finally, FIG. 9 (e) shows a measurement card 37 which provides printed spots which can be darkened with a pen or marker to record the width measurements in a convenient, easy-to-use manner, numbers that may be circled to identify the pin noted in the depth measurement, a space for provision of horse identification data, and the like. After the measurements are recorded, card 37 may be sent to the proprietor of the orthosis for selection of the correct model, or may be used as part of a paper-based, online or electronic selection method.

Figure 10:
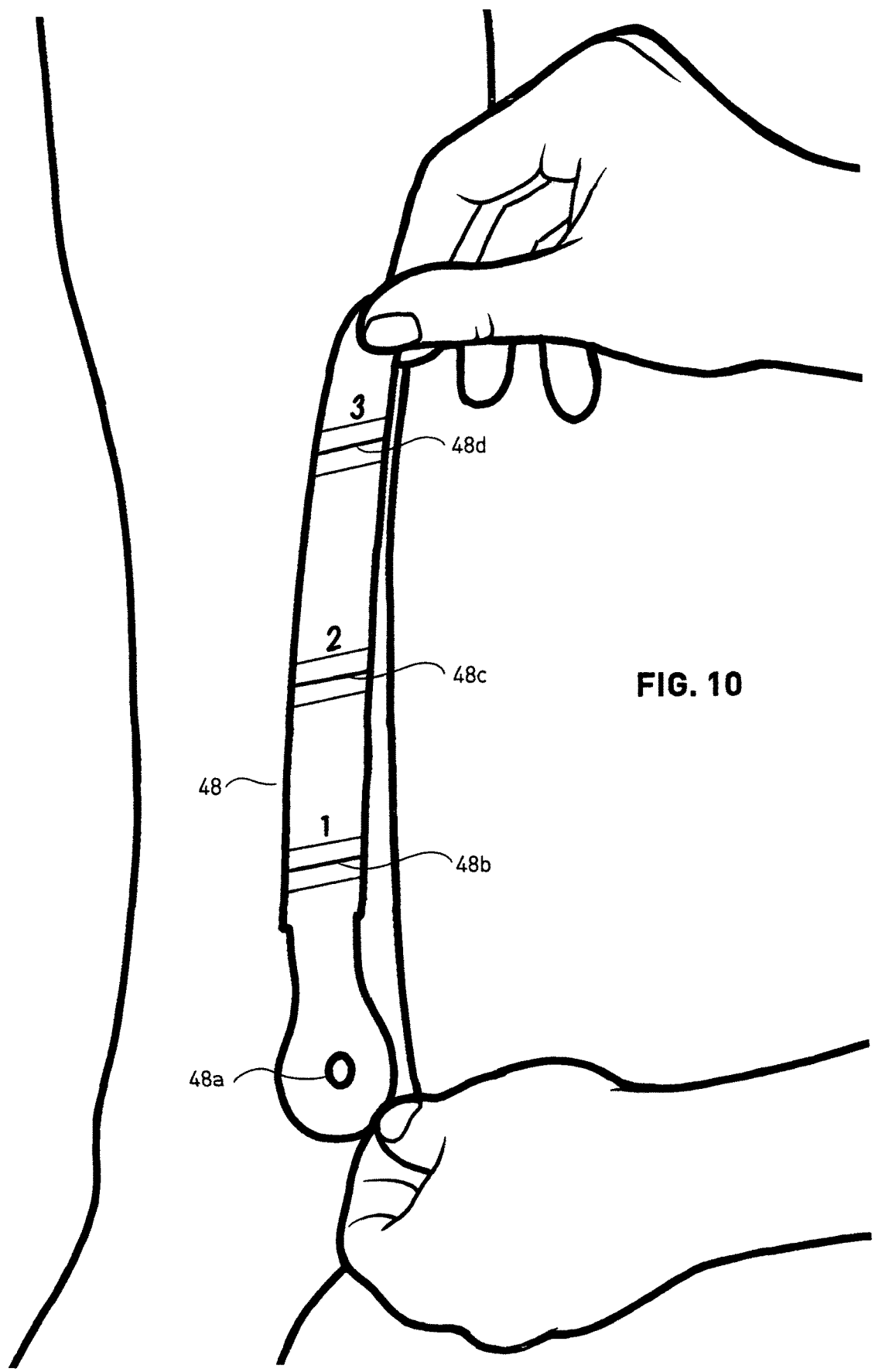
FIG. 10 shows the use of the alignment tape.

The measurement process begins as illustrated by FIG. 10, showing that the alignment tape 48 is secured to the cannon bone such that marker D, locating the COR as discussed above, appears within an aperture 48a in the alignment tape 48. The alignment tape 48 is also preprinted with markings 48b-d indicating predetermined distances from the COR at which the measurements of the cannon bone's width and depth are made; these are referred to as positions 1-3.

FIG. 11, including an enlarged version of the window 36 as FIG. 11(a), illustrates the process of simultaneously measuring the width and depth of the cannon bone. As discussed above, the cannon tool 24 is brought into contact with the cannon bone such that beam 26 contacts the forward surface of the cannon bone at a predetermined distance above the COR, as indicated by the alignment tape 48; in the drawing, the cannon tool 24 is being used to take measurements at position 1 on the alignment tape 48, as indicated by marking 48b. The cannon tool 24 is held level, employing level 32 to confirm this, and square to the central axis of the horse. The anvils 28 and 30 are brought into contact with medial and lateral surfaces of the cannon bone, such that the distance between the anvils is equal to the width X of the cannon bone at position 1. As noted above, this distance could be measured directly using inch or metric markings, but is preferably simply recorded as a color value.

More particularly, as illustrated in FIG. 9(a), the beam is provided with three sets each of four colored areas, corresponding to positions 1-3 on the alignment tape. These are indicated as "colors 1-4", as colors cannot be used in patent drawings; in the preferred embodiment, these are four different colors. When a measurement is made, the color under the line 36a in window 36 corresponding to the position at which the measurement is made is noted, and the corresponding spot on the measurement card 37 darkened. In the example shown in FIG. 11(a), color #1 is under the line 36a opposite the marking corresponding to position 1, and the corresponding spot on the measurement card 37 in FIG. 9(e) has been darkened.

At the same time, the spring-biased pins 34 are in contact with the lateral outer surface of the cannon bone, and one of these will protrude more than the others, corresponding to the depth of the cannon, that is, its widest point. In FIG. 11, this is pin 3. The corresponding pin number has been circled on the measurement card 37. It will be appreciated that the pins 34 could be omitted, and the sliding anvil 30 be provided with numbered markings corresponding to the numbers of the pins shown, so that the depth of the maximum width of the cannon bone could be identified by noting the marking corresponding thereto, e.g., by eye or touch. However, the pins 34 make this identification more positive.

It will be appreciated that the cannon tool 24 is thus capable of making measurements in two dimensions simultaneously, that is, the width X of the cannon bone and the depth Y at which its maximum width is located.

The same procedure is then repeated at positions 2 and 3 as defined by markings 48c and 48d on the alignment tape 48, and the results recorded similarly on the measurement card 37.

As illustrated, the positions of the colors on the beam are offset with respect to one another at positions 1, 2 and 3. This is done corresponding to the variation in width of the cannon bone with distance from the COR; the cannon bone narrows near its midpoint as compared to its ends.

Figures 12, 12A:
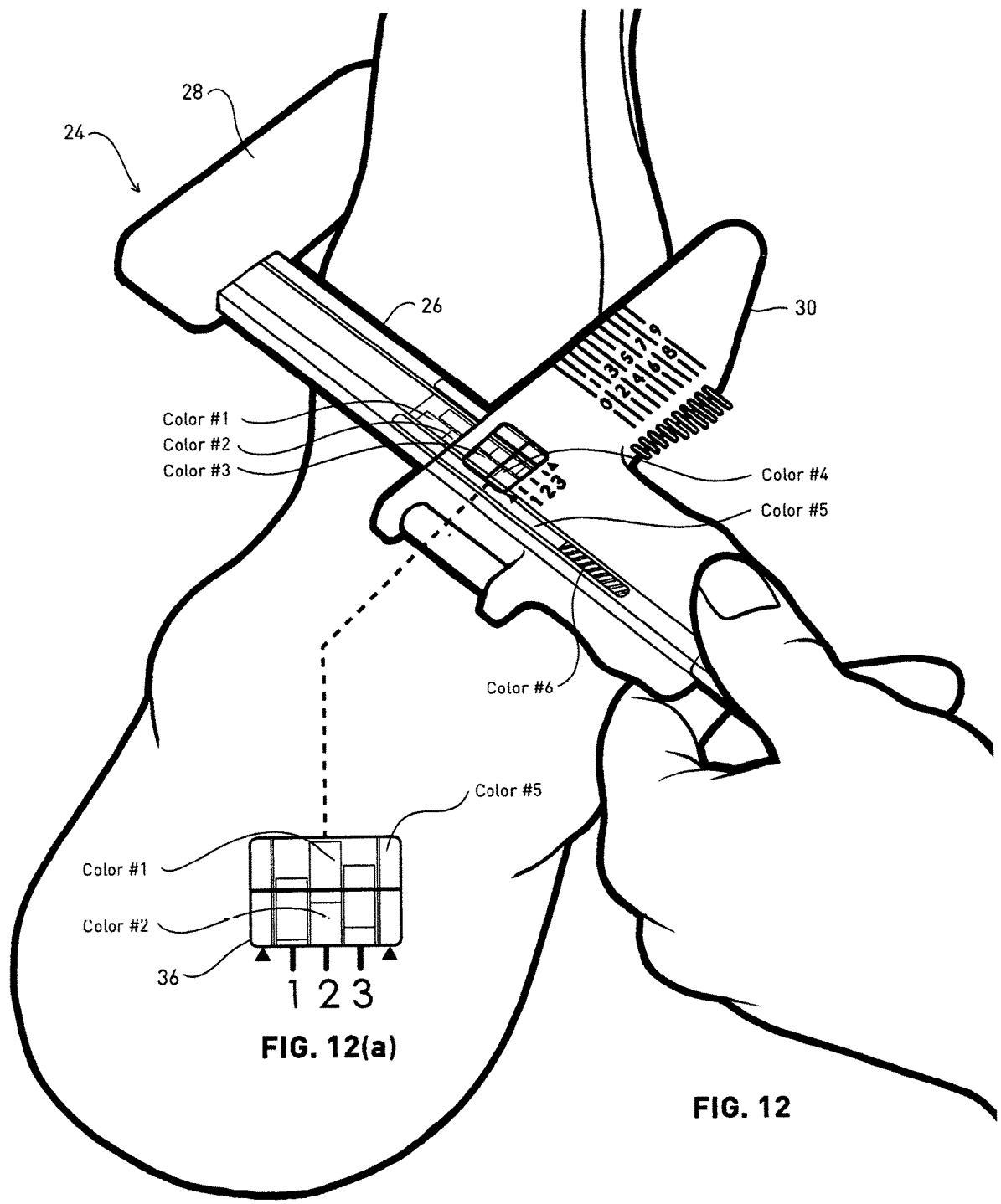
FIG. 12 is a view comparable to FIG. 11, showing the cannon tool in use to measure the width of the left fore fetlock, and includes in FIG. 12 (a) an enlarged plan view of the measurement screen.

The cannon tool 24 is then used to measure the width of the fetlock by placing the opposed anvils against the fetlock at the height of the COR, as illustrated in FIG. 12, including an enlarged view of the window 36 in FIG. 12 (a). In this case, the width is measured by noting the position of line 36a to one of two colors, #5 and #6, provided along the edges of the beam 26, as shown in FIG. 9 (a). In the example of FIG. 12, the line 36a is disposed over color #5, and the corresponding spot on the measurement card of FIG. 9(e) has been darkened. This measurement is used to determine whether the orthosis is to be wide or narrow.

Figure 13:
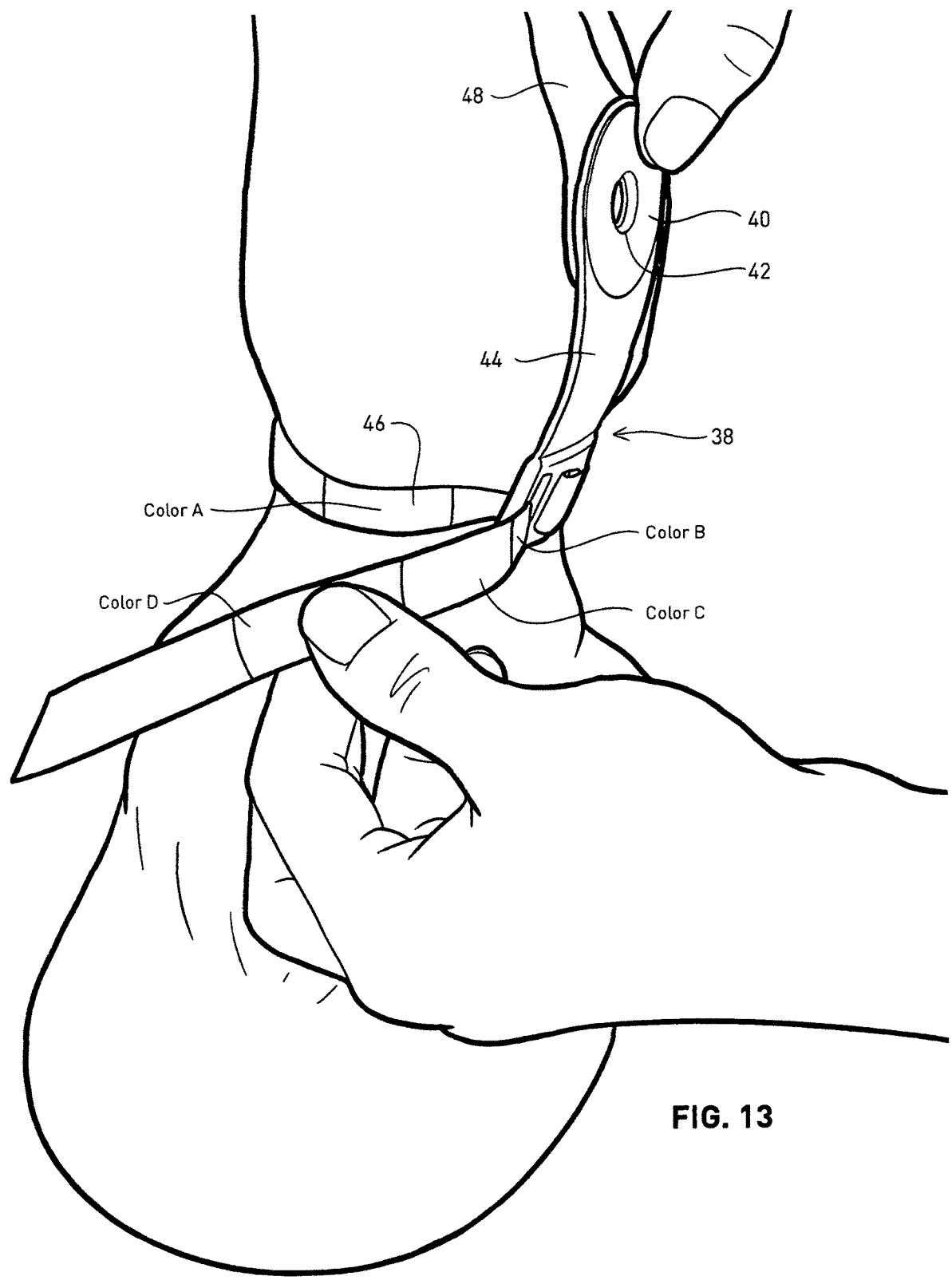
FIG. 13 is a perspective view of the pastern tool in use to measure the circumference of the left fore pastern.

The final step in taking the measurements is measurement of the pastern circumference. This is done as illustrated in FIG. 13. The pastern tool 38 described above is affixed to the alignment strip 48 so that the aperture 42 in the pastern tool is disposed over the COR; mating hook and loop fasteners or the like may be provided thereon for convenience. The tongue 44 extends downwardly, over the fetlock, defining the distance Z between the COR and the point on the pastern at which the circumference is measured. The ribbon 46 is pulled around the pastern snugly. Ribbon 46 is provided with four colored sections, A-D, as indicated. That which is located opposite a marker 50 (FIG. 9(b)) is taken as the measurement, and is recorded on the measurement card 37. In the example of FIG. 13, color B is thus chosen, and the corresponding spot on measurement card 37 has been darkened.

The same process is then performed on the other leg, as the orthoses are generally used in pairs. As noted, the cannon tool is provided with measurement windows and colored patches on both sides, so that the tool can simply be flipped over and used on the opposite leg. As shown by FIG. 9 (e), the measurement card 37 is provided with duplicate spots for entry of the same measurements for both legs.

The measurement card 37 is then, for example, forwarded to the provider of the orthoses, who chooses the appropriate orthoses from the stock of models and provides these to the user, typically a veterinarian. Other options include ordering the orthoses employing a manual look up table, a phone app, or an online selection webpage. As discussed above, where the width of the cannon bone varies along its length, the maximal width is used to select the correct orthosis.

The final step is fitting the orthosis to the individual. As noted above, the measurement steps above are used to select the closest-fitting orthoses from a considerable number of models. The final fitting is performed by heating an inner layer 22 (FIG. 2) of a thermoformable foam material, for example ethylene vinyl acetate (EVA), of the proximal and distal cuffs, to the point that it can be compressed around the cannon and pastern bones, and clamping the orthosis on the fetlock in place using the straps 15 and 16. As the EVA cools it takes the shape of the cannon and pastern bones, ensuring a very good fit of the orthosis to the fetlock.

Figure 14:
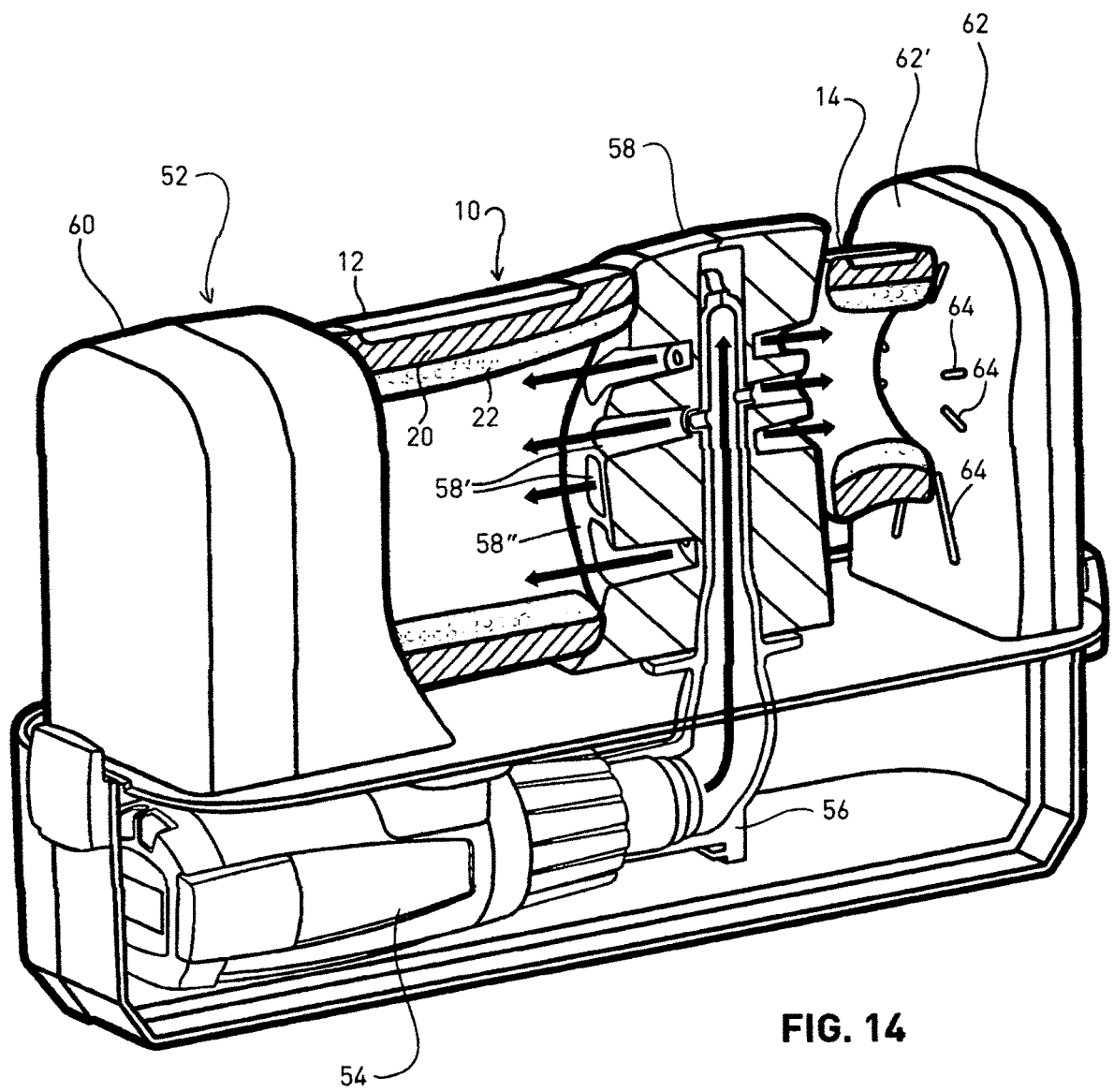
FIG. 14 is a perspective, partially-cutaway view of the heater to which the present application is specifically directed, the heater being used to heat the orthosis prior to final fitting to an individual, and shows the orthosis in position for being heated.

FIG. 14 shows a heating device 52 according to the present invention that is particularly adapted for heating the orthosis as described above. Heating device 52 comprises a heating assembly 54 of a heating element and a fan, providing a stream of hot air via ducting 56 to a perforated plenum 58 defining a number of outlet ducts 58', which provide a number of air streams indicated by arrows in FIG. 14. In use, the orthosis 10 is placed over the plenum 58, so that the cannon cuff 12 is confined between plenum 58 and a first platen 60, and the pastern cuff 14 between plenum 58 and a second platen 62, defining substantially closed cavities. The width of the plenum is selected in correspondence with the space between the cannon and pastern cuffs defined by the pivot structure. All of the various sizes of the orthosis have the same longitudinal dimensions, so that the same heater can be used to fit any size of orthosis. However, it would be within the skill of the art to make the platens relatively movable with respect to the plenum if it were desired to accomodate orthoses of differing dimension or to change the degree of sealing between the corresponding surfaces. Plenum 58, platens 60 and 62, and ducting 56 may all be molded of glass-fiber reinforced nylon, of the grade known in the art as nylon 6, 6.

The hot air heats the EVA foam 22 to a desired temperature, typically 250° F., at which point the orthosis 10 can be removed from the heating device 52 and promptly clamped around the fetlock, as described above, so that the EVA layers 22 in the proximal and distal cuffs conform to the shapes of the cannon and pastern, respectively. The temperature of the surface of the EVA layers 22, and/or the air temperature within the inner cavities may be measured and used to control the operation of the heating assembly, or a timer may be employed to ensure adequate heating.

Geometric features, such as ribs 64, are shown on the inner surface 62' of platen 62, juxtaposed to the pastern cuff 14. These features, which if implemented as ribs 64, may be on the order of ⅛-¼" in height, space the end of the pastern cuff 14 from the platen 62, providing a controlled exit for air flowing from plenum 58, that is, between the end of the generally cylindrical pastern cuff 14 and platen 62. Similar geometric features (not shown) may be provided for the same purpose on the surface (not shown) of platen 60 juxtaposed to the cannon cuff 10, and on the surface (not shown) of plenum 58 juxtaposed to the pastern cuff of the orthosis 10. However, in a preferred embodiment, no such features are provided on the surface 58" of the plenum 58 juxtaposed to the cannon cuff 12. Thus, in this embodiment the surface 58" of the plenum 58 is relatively sealed to the cannon cuff 12, while the surface of the cannon cuff juxtaposed to the platen 60 is spaced therefrom by ribs 64, and the surfaces of plenum 58 and platen 62 are both spaced from the pastern cuff 14, providing controlled leakage of hot air flowing from plenum 58. In general, all of the surfaces that are juxtaposed to the orthosis during the heating step may or may not have geometric features as needed to govern the flow of air in order to produce relatively uniform heating. The contoured shapes of the plenum and platen surfaces relative to the mating contours at the ends of the padding also control the amount of air leakage. In order to limit the escape of hot air from the openings at the rear of the cuffs that are necessary to allow the orthosis to slip over the fetlock, these openings may be closed during heating using the straps and overwrapped with Velcro closures. However, the hot air flows at sufficiently high velocity from ducts 58' that most of the flow is in the vicinity of the inner surface of the cuffs, providing efficient heating.

Noting that the interior volume of the cannon cuff 12 is substantially greater than that of the pastern cuff 14, due to their differing axial lengths, the differing degrees of sealing thus provided, together with the detailed design of ducts 58' in plenum 58, are cooperatively selected so as to control the flow of air from plenum 58 via ducts 58' so that the flow of air from heating assembly 54 substantially uniformly heats the interior surfaces of thermoformable foam layers 22 of the cannon and pastern cuffs, so that when the orthosis is subsequently clamped over the fetlock the thermoformable members 22 thereof are substantially uniformly formable over the respective leg geometry.

It will be appreciated that by fitting closely over the heating device 52, with the cannon and pastern cuffs in substantially sealed relation with plenum 58 and platens 60 and 62, the orthosis 10 essentially provides two substantially closed volumes over the plenum 58, one each within the volume defined by the cannon and pastern cuffs. In this way, the hot air heats only the interior EVA surface of the cannon and pastern cuffs. By comparison, if the orthosis were to be heated, for example, in an oven, it would be heated throughout, including its exterior surface, which would be inconvenient for handling, and would require a great deal of additional energy. Similarly, heating the orthosis by supplying hot air to one end would not promote uniform heating of the inner surface.

While a preferred embodiment of the invention has been described in detail, further improvements and modifications will occur to those of skill in the art, and these are within the scope of the invention where not excluded by the following claims.

What is claimed is:

1. A heating apparatus for heating the interior surface of an orthosis, said orthosis comprising proximal and distal cuffs joined to and spaced from one another by a pivot structure, said cuffs each being of generally cylindrical configuration defining first and second ends and with an open side to allow the cuffs of the orthosis to be disposed over a body joint, and each cuff comprising an outer shell and an inner layer of thermoformable foam, said heating apparatus comprising a source of a stream of hot air, a central plenum and first and second platens, said first and second platens being spaced axially from said plenum, such that said orthosis can be assembled within said heating apparatus, with the plenum disposed between said proximal and distal cuffs, and said proximal and distal cuffs fitting between said plenum and said first and second platens, whereby said first and second ends of said proximal and distal cuffs are juxtaposed to surfaces of said plenum and said platens so as to be in generally sealing relationship therewith, and said plenum being connected to said source of a stream of hot air, and defining a plurality of ducts in communication with interior volumes defined by the interior surfaces of said proximal and distal cuffs and said surfaces of said plenum and said platens juxtaposed thereto.

2. The heating apparatus of claim 1, wherein the degree of sealing between said first and second ends of said proximal and distal cuffs juxtaposed to surfaces of said plenum and said platens is selected in conjunction with said interior volumes and said ducts such that the interior surfaces of said proximal and distal cuffs are heated to a substantially equal degree.

3. The heating apparatus of claim 2, wherein the degree of sealing provided between said proximal and distal cuffs and said surfaces of said plenum and said platens juxtaposed thereto is controlled by provision of geometric features on selected surfaces of said plenum and said platens in order to provide a degree of air leakage therebetween.

4. The heating apparatus of claim 1, wherein the cuffs of the orthosis each further comprise a first intermediate layer of molded foam between the outer shell and the inner layer of thermoformable foam, said intermediate layer being contoured to fit the body joint.

* * * * *